(12) United States Patent
Choe et al.

(10) Patent No.: US 11,732,062 B2
(45) Date of Patent: Aug. 22, 2023

(54) MODIFICATION POLYMERIZATION INITIATOR AND METHOD FOR PREPARING THE SAME

(71) Applicant: LG Chem, Ltd., Seoul (KR)

(72) Inventors: Dong Cheol Choe, Daejeon (KR); Jae Hoon Choe, Daejeon (KR); Hyeon Hui Kim, Daejeon (KR); Jong Young Choi, Daejeon (KR); Jung Yong Lee, Daejeon (KR); Won Jae Lee, Daejeon (KR)

(73) Assignee: LG Chem, Ltd.

( * ) Notice: Subject to any disclaimer, the term of this patent is extended or adjusted under 35 U.S.C. 154(b) by 663 days.

(21) Appl. No.: 16/756,001

(22) PCT Filed: Mar. 15, 2019

(86) PCT No.: PCT/KR2019/003073
§ 371 (c)(1),
(2) Date: Apr. 14, 2020

(87) PCT Pub. No.: WO2019/177436
PCT Pub. Date: Sep. 19, 2019

(65) Prior Publication Data
US 2020/0299419 A1 Sep. 24, 2020

(30) Foreign Application Priority Data

Mar. 16, 2018 (KR) .................. 10-2018-0031026
Mar. 16, 2018 (KR) .................. 10-2018-0031027

(51) Int. Cl.

| *C08F 2/60* | (2006.01) |
| *C08F 2/44* | (2006.01) |
| *C07C 211/21* | (2006.01) |
| *C07C 211/22* | (2006.01) |
| *C07D 207/06* | (2006.01) |
| *C07D 211/14* | (2006.01) |
| *C07D 223/04* | (2006.01) |
| *C07D 241/04* | (2006.01) |
| *C07D 265/30* | (2006.01) |
| *C07F 1/02* | (2006.01) |

(52) U.S. Cl.
CPC .............. *C08F 2/60* (2013.01); *C07C 211/21* (2013.01); *C07C 211/22* (2013.01); *C07D 207/06* (2013.01); *C07D 211/14* (2013.01); *C07D 223/04* (2013.01); *C07D 241/04* (2013.01); *C07D 265/30* (2013.01); *C08F 2/44* (2013.01); *B01J 2219/00033* (2013.01); *B01J 2219/00164* (2013.01); *C07F 1/02* (2013.01)

(58) Field of Classification Search
CPC . C08F 2/60; C08F 2/44; C07C 211/21; C07C 211/22; C07D 207/06; C07D 211/14; C07D 241/04; C07D 265/03; C07D 223/04
See application file for complete search history.

(56) References Cited

U.S. PATENT DOCUMENTS

| 4,397,994 A | 8/1983 | Takeuchi et al. |
| 5,491,230 A | 2/1996 | Lawson et al. |
| 2003/0139563 A1 | 7/2003 | Brockmann et al. |
| 2003/0162978 A1 | 8/2003 | Brockmann et al. |
| 2003/0216522 A1 | 11/2003 | Oshima et al. |
| 2016/0159957 A1 | 6/2016 | Choi et al. |
| 2018/0056716 A1 | 3/2018 | Lee et al. |
| 2018/0208684 A1 | 7/2018 | Choe et al. |
| 2020/0079797 A1 | 3/2020 | Lee et al. |

FOREIGN PATENT DOCUMENTS

| CN | 105473624 A | 4/2016 | |
| CN | 107614506 A | 1/2018 | |
| JP | 2003292529 A | 10/2003 | |
| JP | 2004513087 A | 4/2004 | |
| JP | 3748277 B2 | 2/2006 | |
| JP | 2018517022 A | 6/2018 | |
| JP | 2018522111 A | 8/2018 | |
| JP | 2020515674 A | 5/2020 | |
| KR | 20150056484 A | 5/2015 | |
| KR | 20160092227 A | 8/2016 | |
| RU | 2264414 C1 | 11/2005 | |
| WO | 2017047923 A1 | 3/2017 | |
| WO | WO-2017047923 A1 * | 3/2017 | ............ B01F 5/0604 |

OTHER PUBLICATIONS

Tavtorkin et al., "Coordination Copolymerization of Butadiene with Polar Diene Monomers Based on Myrcene," Polymer Science, Series B: Chemistry (2018) vol. 60, No. 6, pp. 699-707. (Year: 2018).*
Honda et al., Highly stereocontrolled synthesis of isomeric pairs of di- and trisubstituted olefins through [2, 3] sigmatropic rearrangement of allyldimethylammonium methylides, Journal of American Chemical Society, 1990, vol. 112, No. 5, pp. 1999-2001 (Year: 1990).*
Search Report dated Dec. 22, 2021 from Office Action for Chinese Application No. 201980003450.7 dated Jan. 10, 2022. 2 pgs.

(Continued)

*Primary Examiner* — Robert D Harlan
(74) *Attorney, Agent, or Firm* — Lerner David LLP

(57) ABSTRACT

The present invention relates to a modification polymerization initiator and a method for preparing the same, and the modification polymerization initiator includes a derived unit from a compound represented by Formula 1 and may include various functional groups in a molecule, and thus, may initiate polymerization reaction and introduce a functional group into a polymer chain at the same time. In addition, the preparation method according to the present invention may prepare the modification polymerization initiator with high purity in high yield.

15 Claims, No Drawings

(56) References Cited

OTHER PUBLICATIONS

Honda, K. et al., "Highly stereocontrolled syntheses of isomeric pairs of di- and trisubstituted olefins through [2,3] sigmatropic rearrangement of allyldimethylammonium methylides", Journal of the American Chemical Society, Jan. 2, 1990, vol. 112, No. 5, pp. 1999-2001.
International Search Report for Application No. PCT/KR2019/003073 dated Jun. 24, 2019, 2 pages.
A. N. Tavtorkin, et al, "Coordination Copolymerization of Butadiene with Polar Diene Monomers Based on Myrcene", Polymer Science, Series B: Chemistry, issued Nov. 2018, vol. 60, No. 6, pp. 699-707.

* cited by examiner

MODIFICATION POLYMERIZATION INITIATOR AND METHOD FOR PREPARING THE SAME

CROSS-REFERENCE TO RELATED APPLICATIONS

The present application is a national phase entry under 35 U.S.C. § 371 of International Application No. PCT/KR2019/003073 filed Mar. 15, 2019, which claims priority from Korean Patent Application No. 10-2018-0031026 filed Mar. 16, 2018 and Korean Patent Application No. 10-2018-0031027 filed Mar. 16, 2018, all of which are incorporated herein by reference.

TECHNICAL FIELD

The present invention relates to a modification polymerization initiator which is capable of initiating polymerization reaction and introducing a functional group into a polymer chain at the same time, and a method for preparing the same.

BACKGROUND ART

According to the recent demand for cars having a low fuel consumption ratio, a conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based polymers or copolymers such as styrene-butadiene rubbers (hereinafter, referred to as "SBR") and butadiene rubbers (hereinafter, referred to as "BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled by coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

In case where the solution-polymerized SBR (hereinafter, referred to as "SSBR") is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature.

The SSBR is prepared by using an anionic polymerization initiator and is being used by coupling or modifying the chain terminals of the polymer thus formed using various modifiers. For example, U.S. Pat. No. 4,397,994 discloses a method of coupling active anions of the chain terminals of a polymer obtained by polymerizing styrene-butadiene using alkyllithium which is a monofunctional initiator in a non-polar solvent, using a binder such as a tin compound.

Meanwhile, the solution polymerized SSBR is prepared using an anionic polymerization initiator, and in this case, the anionic polymerization initiator mostly uses an organolithium compound. The organolithium compound may be used as it is or after modifying to a functional group-containing compound which is capable of imparting a polymer chain with the functional group. For example, there is a method of preparing and using a modification polymerization initiator having a styrene-based structure unit, a conjugated diene-based structure unit or an arylamine structure unit by reacting a styrene-based compound, a conjugated diene-based compound or an arylamine compound with an organolithium compound, but this method is not economically feasible and has limitation in industrial use. Particularly, the obtain of a modification polymerization initiator using the conjugated diene-based compound is difficult, because the coupling of a functional group with a conjugated diene-based unit is not easy.

For example, JP3748277 discloses an anionic polymerization initiator prepared by reacting an additive in which a nitrogen of a cyclic secondary amine is bonded with conjugated diene carbon, with an organolithium compound. However, in case of preparing by the reaction, the cyclic secondary amine remains to act as a scavenger in the reaction, thereby degrading the yield of the anionic polymerization initiator, and accordingly, filtering and purifying processes are definitely required after the reaction. Accordingly, the development of a modification polymerization initiator which is economically feasible and has excellent industrial use, is required.

In another example, a hexamethylene lithium initiator prepared by the reaction of hexamethyleneimine (MHI) and n-butyllithium (BuLi) as shown in the following Reaction 1 is widely known as a modification polymerization initiator used for preparing SSBR:

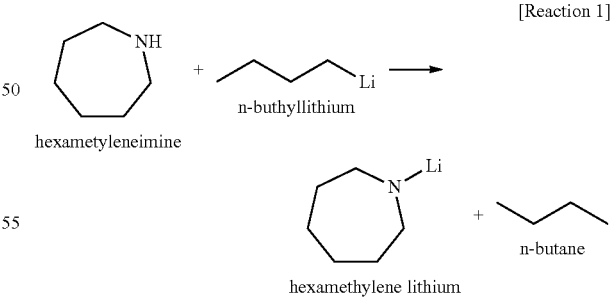

[Reaction 1]

However, the hexamethylene lithium initiator has low solubility with respect to a solvent and is precipitated over time and has a limitation in that reactivity with respect to n-butyllithium is not good though used as a polymerization initiator. In addition, in order to compensate the limitation of the hexamethylene lithium initiator, a method for preparing a modification polymerization initiator by further reacting the hexamethylene lithium synthesized in Reaction 1 with a conjugated diene compound such as isoprene and 1,3-butadiene as in the following Reaction 2 has been suggested:

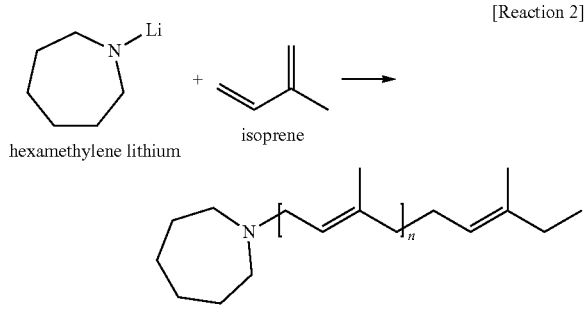

hexamethylene lithium    isoprene

[Reaction 2]

However, though the modification polymerization initiator thus prepared has improved solubility and reactivity when compared with the hexamethylene lithium initiator, precipitation still takes place over time and deactivation arises.

Meanwhile, an anionic polymerization initiator such as the above-described modification polymerization initiator is generally prepared through a batch type process, or an anionic polymerization initiator and SSBR are simultaneously prepared in one batch type reactor. In the former, the anionic polymerization initiator thus prepared necessarily requires a storage step prior to use for preparing SSBR, and reacts with various scavengers such as humidity and air during storage time to lose activity. As a result, the initiator has adverse effects on a subsequent process and may become a factor degrading the physical properties of the SSBR finally prepared. In the latter, the preparation reaction of an anionic polymerization initiator and SSBR polymerization reaction are performed in the same batch type reactor, and the defects relating to the storage may be solved but it is difficult to confirm if the anionic polymerization initiator is properly synthesized and the physical properties of the SSBR finally prepared are inferior to a case of adding a pre-synthesized anionic polymerization initiator. Further, in the conventional batch type process, by-products may be produced by the direct injection, mixing and reaction of raw materials, or unreacted materials may be produced by reverse reaction, and as a result, there are problems of decreasing yield.

Accordingly, recently, in order to solve the problems of the batch type reactor, a method of using a continuous type reactor is being studied.

For example, Korean Laid-open Patent Publication No. 10-2016-0092227 discloses a method for preparing an anionic polymerization initiator using a continuous type reactor including a static mixer. In case of the method, since concentration distribution of raw materials or temperature distribution may become uniform, lithiation reaction is continuously carried out, and problems relating to storage and problems of decreasing yield may be reduced, but with the use of the static mixer, the problem of the exothermic reaction of the lithiation reaction is not solved, and a special cooling apparatus is required to increase preparation cost.

DISCLOSURE OF THE INVENTION

Technical Problem

The present invention is devised to solve the above-mentioned problems of the conventional technique, and an object is to provide a modification polymerization initiator which is used in polymerization reaction to easily initiate reaction and provide a polymer with a functional group having affinity with a filler.

In addition, another object of the present invention is to provide a method for preparing a modification polymerization initiator by which the above-described modification polymerization initiator may be prepared in a high conversion ratio by minimizing side reactions.

Technical Solution

To solve the above-described tasks, the present invention provides a modification polymerization initiator including at least one derived unit from a compound represented by the following Formula 1 and a derived unit from a compound represented by the following Formula 2:

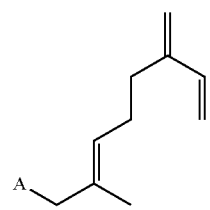

[Formula 1]

in Formula 1,

A is —$NR_aR_b$, —$OR_c$, or —$SR_d$, and $R_a$ to $R_d$ are each independently an alkyl group of 1 to 30 carbon atoms, an alkenyl group of 2 to 30 carbon atoms, an alkynyl group of 2 to 30 carbon atoms, a cycloalkyl group of 2 to 30 carbon atoms, an aryl group of 3 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of $R_a$ to $R_d$ is unsubstituted or substituted with a substituent including one or more heteroatoms selected among N, O, S, Si and F atoms, and $R_a$ and $R_b$ may be combined with each other to form an aliphatic hydrocarbon ring of 5 to 20 carbon atoms, an aromatic hydrocarbon ring of 6 to 20 carbon atoms, or a heterocycle of 3 to 20 carbon atoms, which is unsubstituted or substituted with an alkyl group of 1 to 30 carbon atoms, $$M—R_e$$ [Formula 2]

in Formula 2,

M is an alkali metal, and $R_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

In addition, the present invention provides a method for preparing the modification polymerization initiator, including a step of reacting a compound represented by the following Formula 1 and a compound represented by the following Formula 2:

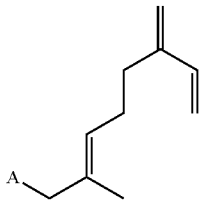

[Formula 1]

in Formula 1,

A is —NR$_a$R$_b$, —OR$_c$, or —SR$_d$, and

R$_a$ to R$_d$ are each independently an alkyl group of 1 to 30 carbon atoms, an alkenyl group of 2 to 30 carbon atoms, an alkynyl group of 2 to 30 carbon atoms, a cycloalkyl group of 2 to 30 carbon atoms, an aryl group of 3 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of R$_a$ to R$_d$ is unsubstituted or substituted with a substituent including one or more heteroatoms selected among N, O, S, Si and F atoms, and R$_a$ and R$_b$ may be combined with each other to form an aliphatic hydrocarbon ring of 5 to carbon atoms, an aromatic hydrocarbon ring of 6 to 20 carbon atoms, or a heterocycle of 3 to 20 carbon atoms, which is unsubstituted or substituted with an alkyl group of 1 to 30 carbon atoms, M—R$_e$        [Formula 2]

in Formula 2,

M is an alkali metal, and

R$_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

Advantageous Effects

The modification polymerization initiator according to the present invention includes a derived unit from a compound represented by Formula 1 and may include various functional groups in a molecule, and thus, may initiate polymerization reaction and introducing a functional group into a polymer chain at the same time.

In addition, the preparation method according to the present invention may easily prepare a modification polymerization initiator which is used in the polymerization reaction of a polymer to initiate polymerization easily and provide a polymer with a functional group which has affinity with a filler at the same time. Further, the production of an unreacted material during lithiation reaction may be decreased by performing the preparation method through continuous type reaction using a continuous type reactor, problems due to the exothermic reaction of the lithiation reaction and the generation of by-products may be reduced by rapid removal of heat, and thus, a conversion ratio may be increased and a modification polymerization initiator with high purity may be prepared in high yield.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The term "substituted" used in the present invention may mean that hydrogen of a functional group, atomic group or compound is substituted with a specific substituent, and in case where the hydrogen of the functional group, atomic group or compound is substituted with the specific substituent, one or a plurality of two or more substituents may be present according to the number of hydrogen present in the functional group, atomic group or compound. If a plurality of substituents is present, each substituent may be the same or different.

The term "alkyl group" used in the present invention may mean monovalent aliphatic saturated hydrocarbon, and may include both a linear alkyl group such as methyl, ethyl, propyl and butyl, and a branched alkyl group such as isopropyl, sec-butyl, tert-butyl and neo-pentyl.

The term "alkylene group" used in the present invention may mean divalent aliphatic saturated hydrocarbon such as methylene, ethylene, propylene and butylene.

The term "alkenyl group" used in the present invention may mean an alkyl group including one or two or more double bonds.

The term "alkynyl group" used in the present invention may mean an alkyl group including one or two or more triple bonds.

The term "cycloalkyl group" used in the present invention may mean cyclic saturated hydrocarbon, or cyclic unsaturated hydrocarbon including one or two or more unsaturated bonds.

The term "aryl group" used in the present invention may mean cyclic aromatic hydrocarbon, and may include both monocyclic aromatic hydrocarbon including one ring, and polycyclic aromatic hydrocarbon including two or more bonded rings.

The term "derived unit" and "derived functional group" used in the present invention may represent a component or a structure comes from a certain material, or the material itself.

The present invention provides a modification polymerization initiator which acts as a polymerization initiator for initiating polymerization during polymerizing a polymer, particularly, a conjugated diene-based polymer, and at the same time, acts as a modifier introducing a functional group into a polymer chain.

The modification polymerization initiator according to an embodiment of the present invention is characterized in including a derived unit from a compound represented by the following Formula 1 and a derived unit from a compound represented by the following Formula 2:

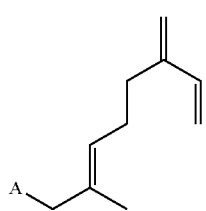

[Formula 1]

in Formula 1,

A is —NR$_a$R$_b$, —OR$_c$, or —SR$_d$, and

R$_a$ to R$_d$ are each independently an alkyl group of 1 to 30 carbon atoms, an alkenyl group of 2 to 30 carbon atoms, an alkynyl group of 2 to 30 carbon atoms, a cycloalkyl group of 2 to 30 carbon atoms, an aryl group of 3 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of R$_a$ to R$_d$ is unsubstituted or substituted with a substituent including one or more heteroatoms selected among N, O, S, Si and F atoms, and R$_a$ and R$_b$ may be combined with each other to form an aliphatic hydrocarbon ring of 5 to carbon atoms, an aromatic hydrocarbon ring of 6 to 20 carbon atoms, or a heterocycle of 3 to 20 carbon atoms, which is unsubstituted or substituted with an alkyl group of 1 to 30 carbon atoms, $$M-R_e \quad \text{[Formula 2]}$$

in Formula 2,

M is an alkali metal, and

R$_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

Particularly, in Formula 1, A is —NR$_a$R$_b$, —OR$_c$, or —SR$_d$, where R$_a$ to R$_d$ may be each independently unsubstituted or substituted with a substituent including one or more heteroatoms selected among N, O, S, Si and F atoms, and in case of being unsubstituted, R$_a$ to R$_d$ may be each independently an alkyl group of 1 to 20 carbon atoms, an alkenyl group of 2 to 20 carbon atoms, an alkynyl group of 2 to 20 carbon atoms, a cycloalkyl group of 3 to 20 carbon atoms, an aryl group of 6 to 20 carbon atoms, a heteroalkyl group of 1 to 20 carbon atoms, a heteroalkenyl group of 2 to carbon atoms, a heteroalkynyl group of 2 to 20 carbon atoms, a heterocycloalkyl group of 2 to 20 carbon atoms or a heteroaryl group of 3 to 20 carbon atoms. In addition, R$_a$ and R$_b$ in —NR$_a$R$_b$ may be combined with each other to form an aliphatic hydrocarbon ring of 5 to 10 carbon atoms, an aromatic hydrocarbon ring of 6 to 10 carbon atoms, or a heterocycle of 3 to 10 carbon atoms, which is unsubstituted or substituted with an alkyl group of 1 to 10 carbon atoms, where the heterocycle may be a ring group in which one or more carbon atoms forming the ring is substituted with heteroatoms, and the heteroatom may be one or more selected among N, O, S, Si and F atoms.

More particularly, in Formula 1, A may be selected from substituents represented by the following Formula 1a to Formula 1c:

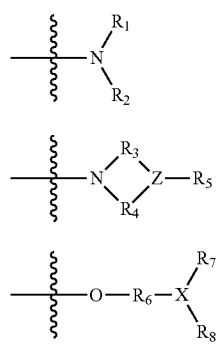

[Formula 1a]

[Formula 1b]

[Formula 1c]

in Formula 1a to Formula 1c,

R$_1$, R$_2$, R$_5$, R$_7$ and R$_8$ are each independently an alkyl group of 1 to 10 carbon atoms, an alkenyl group of 2 to 10 carbon atoms, an alkynyl group of 2 to 10 carbon atoms, a cycloalkyl group of 3 to 10 carbon atoms, an aryl group of 3 to 10 carbon atoms, a heteroalkyl group of 1 to 10 carbon atoms, a heteroalkenyl group of 2 to 10 carbon atoms, a heteroalkynyl group of 2 to 10 carbon atoms, a heterocycloalkyl group of 2 to 10 carbon atoms, or a heteroaryl group of 3 to 10 carbon atoms, where R$_1$ and R$_2$, and R$_7$ and R$_8$ may be each independently combined to form an aliphatic hydrocarbon ring of 5 to 20 carbon atoms or an aromatic hydrocarbon ring of 6 to 20 carbon atoms, and each of R$_1$, R$_2$, R$_5$, R$_7$ and R$_8$ is unsubstituted or substituted with a substituent including one or more heteroatoms selected among N, O and S atoms, R$_3$, R$_4$ and R$_6$ are each independently an alkylene group of 1 to 10 carbon atoms, which is unsubstituted or substituted with a substituent including an alkyl group of 1 to 10 carbon atoms, a cycloalkyl group of 5 to 10 carbon atoms, an aryl group of 6 to 10 carbon atoms, or a heteroatom selected among N and O atoms, and X and Z are each independently one selected among N, O and S atoms, where if X is O or S, R$_8$ is not present, and if Z is O or S, R$_5$ is not present.

Particularly, in Formula 1a to Formula 1c, R$_1$, R$_2$, R$_5$, R$_7$ and R$_8$ are each independently an alkyl group of 1 to 10 carbon atoms, which is unsubstituted or substituted with a substituent including one or more heteroatoms selected among N, O and S atoms, where R$_1$ and R$_2$, and R$_7$ and R$_8$ are each independently combined to form an aliphatic hydrocarbon ring of 5 to 10 carbon atoms or an aromatic hydrocarbon ring of 6 to 10 carbon atoms, R$_3$, R$_4$ and R$_6$ are each independently an alkylene group of 1 to 10 carbon atoms, which is unsubstituted or substituted with an alkyl group of 1 to 6 carbon atoms, R$_5$ is an alkyl group of 1 to 10 carbon atoms, and X and Z are each independently one selected among N, O and S atoms, where if X is O or S, R$_8$ may not be present, and if Z is O or S, R$_5$ may not be present.

More particularly, a myrcene derivative compound represented by Formula 1 may be a compound represented by the following Formula 1-1 to Formula 1-11:

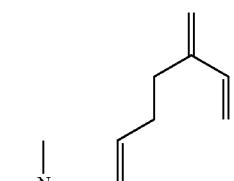

[Formula 1-1]

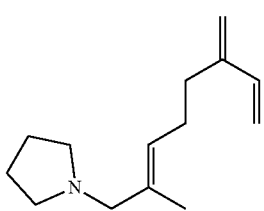

[Formula 1-2]

[Formula 1-3]

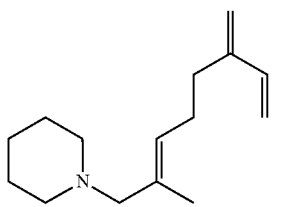

[Formula 1-4]

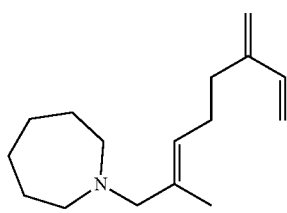

[Formula 1-5]

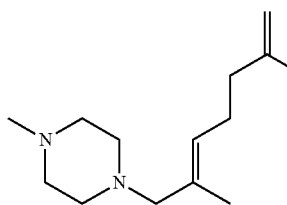

[Formula 1-6]

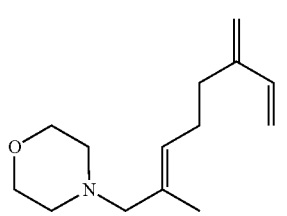

[Formula 1-7]

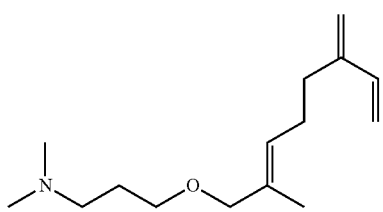

[Formula 1-8]

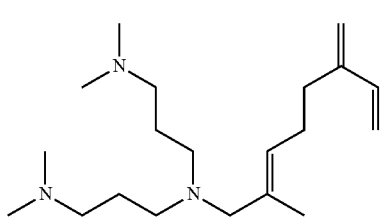

[Formula 1-9]

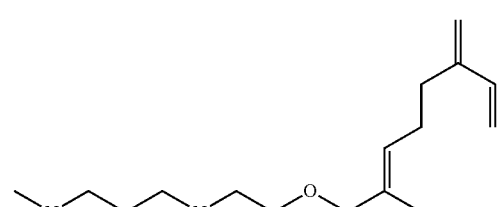

[Formula 1-10]

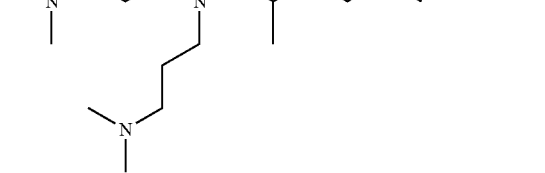

[Formula 1-11]

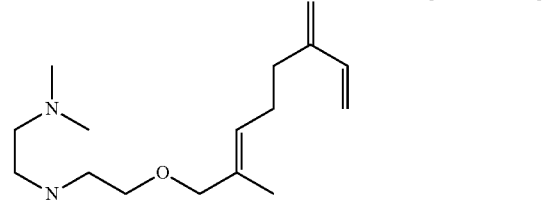

In addition, in Formula 2, M is an alkali metal and $R_e$ may be hydrogen, an alkyl group of 1 to 10 carbon atoms, an alkenyl group of 2 to 10 carbon atoms, an alkynyl group of 2 to 10 carbon atoms, a cycloalkyl group of 5 to 10 carbon atoms or an aryl group of 6 to 10 carbon atoms, particularly, in Formula 2, M may be Na, K or Li and Re may be an alkyl group of 1 to 10 carbon atoms.

In addition, the modification polymerization initiator according to an embodiment of the present invention may be a single material or a mixture type obtained by mixing various materials. Here, the mixture may mean the presence of various isomers together.

Particularly, the modification polymerization initiator may include one or more selected from the group consisting of a compound represented by the following Formula 3 and isomers thereof:

[Formula 3]

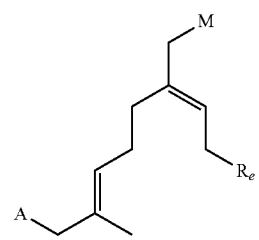

In Formula 3, A is the same as defined in Formula 1, M is Na, K or Li, and $R_e$ is hydrogen or an alkyl group of 1 to 10 carbon atoms. In addition, in Formula 3, M may be bonded to neighboring carbon via an ionic bond.

Meanwhile, the isomer of the compound represented by Formula 3 may include both a structural isomer and a stereoisomer of the compound represented by Formula 3, and for example, a compound represented by the following Formula 3-1 to Formula 3-3:

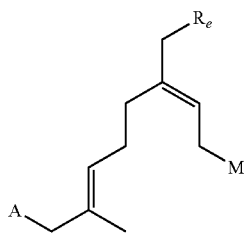

[Formula 3-1]

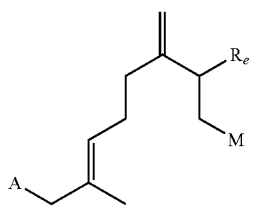

[Formula 3-2]

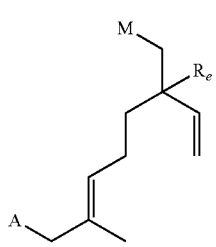

[Formula 3-3]

In Formula 3-1 to Formula 3-3, A, M and $R_e$ are the same as defined in Formula 3.

In addition, the modification polymerization initiator according to an embodiment of the present invention may include one or more selected from a dimer, a trimer and an oligomer of each of the compound represented by Formula 3 and an isomer thereof.

Here, the dimer represents a type in which two derived units from the compound represented by Formula 1 and one derived unit from the compound represented by Formula 2 per molecule, the trimer represents a type in which three derived units from the compound represented by Formula 1 and one derived unit from the compound represented by Formula 2, and the oligomer is a type in which a plurality of derived units from the compound represented by Formula 1 and one derived unit from the compound represented by Formula 2 per molecule.

In addition, the compound represented by Formula 1, according to an embodiment of the present invention may be prepared by reacting myrcene with a functional group compound, for example, may be prepared by one or more methods among two methods of Method 1 and Method 2 below according to substituent A in Formula 1.

[Method 1]

The compound represented by Formula 1, according to an embodiment of the present invention may be prepared through a step of reacting a compound represented by the following Formula 4 and an alkylsulfonyl chloride-based compound in the presence of an organic solvent to prepare a compound represented by the following Formula 5; and a step of reacting the compound represented by Formula 5 and a compound represented by the following Formula 6:

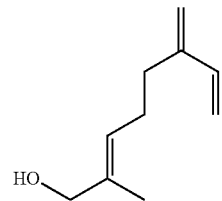

[Formula 4]

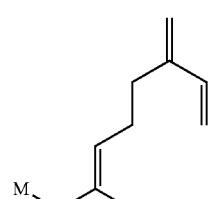

[Formula 5]

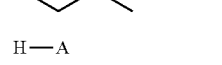

[Formula 6]

In Formulae 5 and 6, A is the same as defined above, and D is a leaving group.

Here, the compound represented by Formula 4 may be prepared, for example, through reaction like the following Reaction 3:

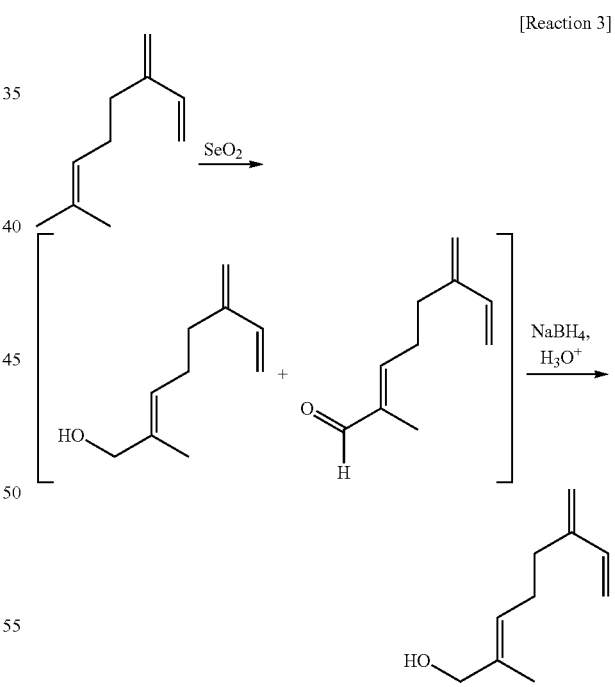

[Reaction 3]

[Method 2]

The compound represented by Formula 1, according to an embodiment of the present invention may be prepared through a step of reacting a compound represented by the following Formula 6 and an alkylsulfonyl chloride-based compound in the presence of an organic solvent to prepare a compound represented by the following Formula 7; and a step of reacting the compound represented by Formula 7 and a compound represented by the following Formula 4:

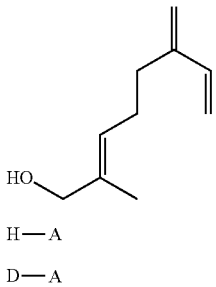
[Formula 4]

H—A [Formula 6]

D—A [Formula 7]

[Formula 1]

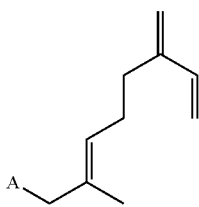

In Formulae 6 and 7, A and D are the same as described above.

In addition, the present invention provides a method for preparing the modification polymerization initiator.

The method for preparing the modification polymerization initiator according to an embodiment of the present invention is characterized in including a step of reacting a compound represented by the following Formula 1 and a compound represented by the following Formula 2:

[Formula 1]

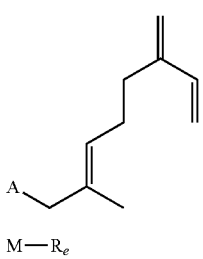

M—$R_e$ [Formula 2]

In Formula 1 and Formula 2, A, M and $R_e$ are the same as defined above.

In an embodiment of the present invention, the compound represented by Formula 1 and the compound represented by Formula 2 may be reacted in a molar ratio of 1:0.5 to 5.0, and the reaction may be performed in a temperature range of 0° C. to 80° C. and in pressure conditions of 0.5 bar to 10 bar.

Meanwhile, in an embodiment of the present invention, the reaction may be performed through batch type or continuous type reaction. In this case, the batch type and the continuous type reaction may be performed in the same conditions except for reaction type, and may be performed in other conditions more suited for each reaction type according to circumstances.

Particularly, if the reaction is performed through the batch type reaction, the compound represented by Formula 1 and the compound represented by Formula 2 may be reacted in a molar ratio of 1:0.5 to 3.0, more particularly, in a molar ratio of 1:1 to 2.

In addition, the compound represented by Formula 1 and the compound represented by Formula 2 may be performed in a temperature range of 0° C. to 45° C. and pressure conditions of an atmospheric pressure or more, particularly, in a temperature range of 20° C. to 30° C. and pressure conditions of 0.5 bar to 2 bar.

In addition, the reaction may be performed in the presence of a polar additive to control the reactivity of the compound represented by Formula 1 and the compound represented by Formula 2. In this case, the polar additive is not specifically limited but may include, for example, one or more selected from the group consisting of tetrahydrofuran, ditetrahydrofurylpropane, diethyl ether, cycloamyl ether, dipropyl ether, ethylene dimethyl ether, ethylene diethyl ether, diethyl glycol, dimethyl glycol, tert-butoxyethoxyethane, bis(3-dimethylamino ethyl) ether, (dimethylamino ethyl) ethyl ether, trimethylamine, triethylamine, tripropylamine and tetramethylethylenediamine. In this case, the polar additive may be used in a molar ratio of 1.0 to 5.0 with respect to 1 mol of the compound represented by Formula 1.

In another embodiment of the present invention, if the reaction is performed through continuous type reaction, the reaction may be performed in a continuous type reactor including a first continuous type channel and a second continuous type channel, and prior to performing the reaction, a first reactant including the compound represented by Formula 1 may be injected through the first continuous type channel to the continuous type reactor and a second reactant including the compound represented by Formula 2 may be injected through the second continuous type channel to the continuous type reactor.

Here, the reaction may be performed in the continuous type reactor. In this case, the continuous type reactor may mean a reactor performing reaction while continuously injecting raw materials used in the reaction.

Particularly, the reaction may be performed in the continuous type reactor including the first continuous type channel and the second continuous type channel, and prior to performing the reaction, the first reactant including the compound represented by Formula 1 may be injected through the first continuous type channel to the continuous type reactor and the second reactant including the compound represented by Formula 2 may be injected through the second continuous type channel to the continuous type reactor. Here, the first continuous type channel and the second continuous type channel may mean injection parts (or inputting parts) for controlling the injection amounts of the first reactant and the second reactant, respectively, in the continuous type reactor, and in this case, the injection amounts of the first reactant and the second reactant may be each independently controlled. Through this, each injection amount may be controlled according to reaction environments and side reactions may be minimized.

In addition, the reaction may be performed in a temperature range of 0° C. to 80° C., or 15° C. to 50° C. and in pressure conditions of 0.5 bar to 10 bar, or 1 bar to 4 bar, and within these ranges, reaction rate may become excellent and side reactions may be minimized.

In addition, the first reactant may be injected through the first continuous type channel in a rate of 1.0 g/min to 20.0 g/min to the continuous type reactor, and the second reactant may be injected through the second continuous type channel in a rate of 1.0 g/min to 20.0 g/min to the continuous type reactor. Particularly, the first reactant may be injected through the first continuous type channel in a rate of 1.5 g/min to 8.5 g/min to the continuous type reactor, and the second reactant may be injected through the second continuous type channel in a rate of 1.5 g/min to 8.5 g/min to the continuous type reactor. Within these ranges, the injection amounts of the compound represented by Formula 1 and the compound represented by Formula 2 may be appropriately controlled without rapid change, thereby minimizing side reactions.

In addition, during the reaction, the compound represented by Formula 1 and the compound represented by Formula 2 may be reacted in a molar ratio of 1:0.5 to 1:5, and particularly, the compound represented by Formula 1 and the compound represented by Formula 2 may be reacted in a molar ratio of 1:0.8 to 1:1.5. If the compound represented by Formula 1 and the compound represented by Formula 2 are reacted in the above-described molar ratio, side reactions may be decreased.

Meanwhile, the first reactant may be a material having flowability so that the compound represented by Formula 1 may be easily injected to the continuous type reactor to participate in the reaction, for example, the first reactant may be the compound represented by Formula 1 itself, or a solution including the compound represented by Formula 1 and a reaction solvent.

In addition, the second reactant may be a material having flowability so that the compound represented by Formula 2 may be easily injected to the continuous type reactor to participate in the reaction, for example, the second reactant may be the compound represented by Formula 2 itself, or a solution including the compound represented by Formula 2 and a reaction solvent.

Here, in case where the first reactant and the second reactant are solutions, the concentration of the solution is not specifically limited and may be controlled so that the compound represented by Formula 1 and the compound represented by Formula 2 may have the above-described molar ratio.

In addition, the reaction solvent may be a hydrocarbon solvent which does not react with anions, for example, one or more selected among a linear hydrocarbon compound such as pentane, hexane and octane; a branched derivative thereof; a cyclic hydrocarbon compound such as cyclohexane and cycloheptane; an aromatic hydrocarbon compound such as benzene, toluene and xylene; and liner or cyclic ethers such as dimethyl ether, diethyl ether, anisole and tetrahydrofuran. Particularly, the reaction solvent may be cyclohexane, hexane, tetrahydrofuran or diethyl ether.

Meanwhile, the reaction according to an embodiment of the present invention may be performed in the presence of a polar additive according to need, and in this case, the polar additive may be injected into the continuous type reactor by being contained in the first reactant or the second reactant, and particularly, the polar additive may be injected into the continuous type reactor by being contained in the first reactant.

That is, the first reactant may include a polar additive, and in this case, the polar additive may be included in the first reactant in a molar ratio of 1.0 to 5.0 with respect to 1 mol of the compound represented by Formula 1. Within this range, the reactivity between the compound represented by Formula 1 and the compound represented by Formula 2 may be appropriately controlled to easily carry out the reaction and decrease side reactions. In this case, the polar additive may be the same as described above.

In case of performing the preparation method of the modification polymerization initiator according to the present invention by continuous type reaction using a continuous type reactor, the yield may be higher than a preparation method through a batch type reaction.

Particularly, in case of performing the continuous type reaction, the mixing ratio of reaction raw materials (for example, the compound represented by Formula 1 and the compound represented by Formula 2) during lithiation reaction may be increased to decrease the production of unreacted material, and the production of by-products may be decreased by reducing problems due to the exothermic reaction of the lithiation reaction by rapid removal of heat. As a result, a conversion ratio may be improved and a modification polymerization initiator with high purity may be stably prepared in high yield.

In addition, since the reaction is continuously carried out by continuously injecting the reaction raw materials, reproducibility may be better than the batch type reaction, and thus, a modification polymerization initiator having a certain performance may be prepared.

Also, the present invention provides a modified conjugated diene-based polymer including a functional group derived from the modification polymerization initiator.

The modified conjugated diene-based polymer according to an embodiment of the present invention includes a repeating unit derived from a conjugated diene-based monomer and may include a functional group derived from the modification polymerization initiator in at least one terminal.

Here, the repeating unit derived from the conjugated diene-based monomer may mean a repeating unit formed during polymerizing a conjugated diene-based monomer, and the conjugated diene-based monomer may be one or more selected from the group consisting of 1,3-butadiene, 2,3-dimethyl-1,3-butadiene, piperylene, 3-butyl-1,3-octadiene, isoprene, 2-phenyl-1,3-butadiene, and 2-halo-1,3-butadiene (halo means a halogen atom).

Meanwhile, the modified conjugated diene-based polymer may be, for example, a copolymer further including a repeating unit derived from an aromatic vinyl-based monomer together with the repeating unit derived from the conjugated diene-based monomer, and the repeating unit derived from the aromatic vinyl-based monomer may mean a repeating unit formed by an aromatic vinyl-based monomer during polymerizing. Here, the aromatic vinyl-based monomer may be, for example, one or more selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl) styrene, and 1-vinyl-5-hexylnaphthalene.

Hereinafter, the present invention will be explained in more detail referring to embodiments. However, the embodiments are provided for illustrating the present invention, and the scope of the present invention is not limited thereto.

EXAMPLE 1

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in hexane) of 2.5 M n-butyllithium, and 6.2 mmol of a compound represented by Formula 1-5 below were injected in order into the reactor, followed by stirring for 1 minute to prepare a modification polymerization initiator including a compound represented by Formula i below. The synthesis of the modification polymerization initiator thus prepared was confirmed by the change of molecular weights between the compound represented by Formula 1-5 and a finally obtained material through GC/MS analysis. From MS analysis results, m/z=292 g/mol, and the molecular weight of the compound represented by Formula 1-5 as a starting material was 234 g/mol. In this case, the GC/MS analysis results of the modification polymerization initiator represented that Li in the modification polymerization initiator was substituted with H.

Particularly, for the GC/MS analysis, ZB-5MS (0.25 mm (ID) ×30 ml, 0.25 μm d.f. capillary) was used as a column, a gas flow rate (column (He)) was 1 ml/min, the oven temperature was initially 50° C., elevated to 320° C. after 3 minutes in a rate of 10° C./min and kept for 15 minutes, the injector temperature was 250° C., a split ratio was 1/20, and an injection amount was controlled to 0.2 μl. In addition, the modification polymerization initiator was measured after quenching for the protonation of an organolithium part.

[Formula 1-5]

[Formula i]

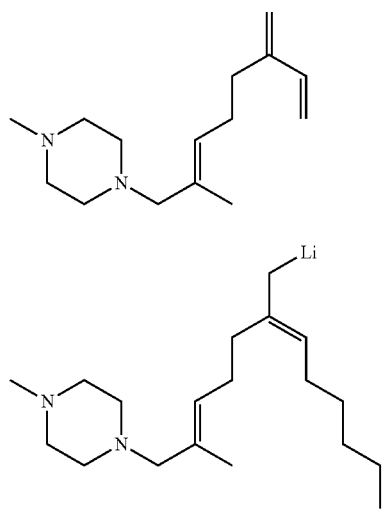

EXAMPLE 2

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 6.2 mmol of a compound represented by Formula 1-7 below were injected in order into the reactor, followed by stirring for 1 minute to prepare a modification polymerization initiator including a compound represented by Formula ii below. The synthesis of the modification polymerization initiator thus prepared was confirmed by the change of molecular weights between the compound represented by Formula 1-7 and a finally obtained material through GC/MS analysis. From MS analysis results, m/z=295 g/mol, and the molecular weight of the compound represented by Formula 1-7 as a starting material was 237 g/mol. In this case, the GC/MS analysis results of the modification polymerization initiator represented that Li in the modification polymerization initiator was substituted with H. GC/MS analysis was performed by the same method as in Example 1.

[Formula 1-7]

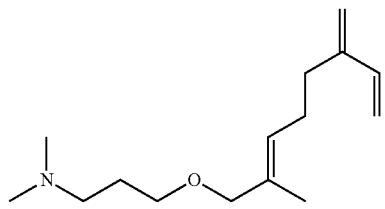

[Formula ii]

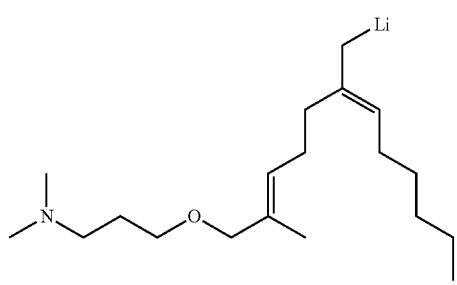

EXAMPLE 3

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 6.2 mmol of a compound represented by Formula 1-6 below were injected in order into the reactor, followed by stirring for 1 minute to prepare a modification polymerization initiator including a compound represented by Formula iii below. The synthesis of the modification polymerization initiator thus prepared was confirmed by the change of molecular weights between the compound represented by Formula 1-6 and a finally obtained material through GC/MS analysis. From MS analysis results, m/z=279 g/mol, and the molecular weight of the compound represented by Formula 1-6 as a starting material was 221 g/mol. In this case, the GC/MS analysis results of the modification polymerization initiator represented that Li in the modification polymerization initiator was substituted with H. GC/MS analysis was performed by the same method as in Example 1.

[Formula 1-6]

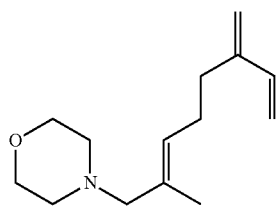

[Formula iii]

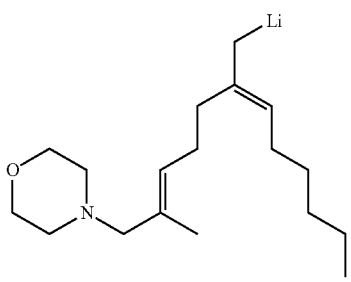

EXAMPLE 4

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 6.2 mmol of a compound represented by Formula 1-1 below were injected in order into the reactor, followed by stirring for 1 minute to prepare a modification polymerization initiator including a compound represented by Formula iv below. The synthesis of the modification polymerization initiator thus prepared was confirmed by the change of molecular weights between the compound represented by Formula 1-1 and a finally obtained material through GC/MS analysis. From MS analysis results, m/z=237 g/mol, and the molecular weight of the compound represented by Formula 1-1 as a starting material was 179 g/mol. In this case, the GC/MS analysis results of the modification polymerization initiator represented that Li in the modification polymerization initiator was substituted with H. GC/MS analysis was performed by the same method as in Example 1.

[Formula 1-1]

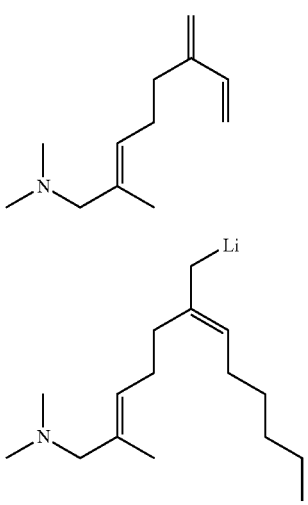

[Formula iv]

EXAMPLE 5

A reactor in an inert state was prepared through purging with nitrogen for a constant time and applying vacuum.

The internal temperature of the reactor was controlled to 25° C. and the internal pressure was controlled to 1 bar, and then, 16.1 g of n-hexane, 0.7 g (6.2 mmol) of tetramethylethyleneamine, 1.7 g (6.2 mmol in n-hexane) of 2.5 M n-butyllithium, and 12.4 mmol of a compound represented by Formula 1-5 below were injected in order into the reactor, followed by stirring for 10 minute to prepare a modification polymerization initiator including a compound represented by Formula v below. The synthesis of the modification polymerization initiator thus prepared was confirmed by the change of molecular weights between the compound represented by Formula 1-5 and a finally obtained material through GC/MS analysis. From MS analysis results, m/z=526 g/mol, and the molecular weight of the compound represented by Formula 1-5 as a starting material was 234 g/mol. In this case, the GC/MS analysis results of the modification polymerization initiator represented that Li in the modification polymerization initiator was substituted with H. GC/MS analysis was performed by the same method as in Example 1.

[Formula 1-5]

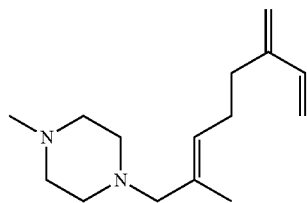

[Formula v]

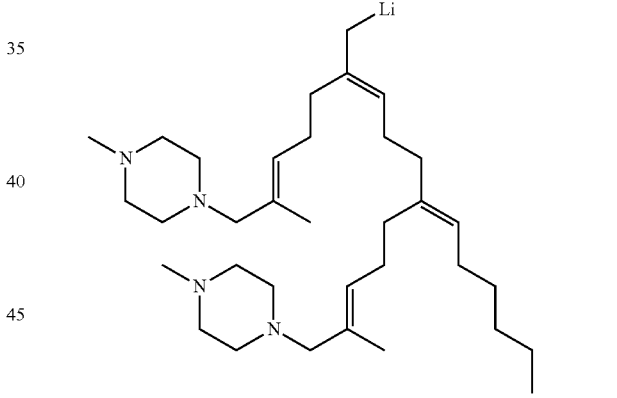

EXAMPLE 6

Two 2 L, vacuum dried stainless steel pressure vessels were prepared. To the first pressure vessel, 1609 g of hexane, 1465 g of a compound represented by Formula 1-5 below, and 103 g of tetramethylethylenediamine were injected to prepare a first reactant. At the same time, to the second pressure vessel, 280 g of 2.5 M n-butyllithium of a liquid phase (in hexane) and 1580 g of hexane were injected to prepare a second reactant. In this case, a molar ratio of the compound represented by Formula 1-5, n-butyllithium and tetramethylethylenediamine was 1:1:1.4. In a state of maintaining the pressure of each pressure vessel to 5 bar, into a continuous type reactor using a mass flowmeter, the first reactant was injected via a first continuous type channel in an injection rate of 1.0 g/min and the second reactant was injected via a second continuous type channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula i below. The synthesis of the modification polymerization initiator thus prepared was confirmed by the change of molecular weights between the compound represented by Formula 1-5 and a finally obtained material through GC/MS analysis. From MS analysis results, m/z=292 g/mol, and the molecular weight of the compound represented by Formula 1-5 as a starting material was 234 g/mol. In this case, the GC/MS analysis results of the modification polymerization initiator represented that Li in the modification polymerization initiator was substituted with H. GC/MS analysis was performed by the same method as in Example 1.

obtained material through GC/MS analysis. From MS analysis results, m/z=295 g/mol, and the molecular weight of the compound represented by Formula 1-7 as a starting material was 237 g/mol. In this case, the GC/MS analysis results of the modification polymerization initiator represented that Li in the modification polymerization initiator was substituted with H. GC/MS analysis was performed by the same method as in Example 1.

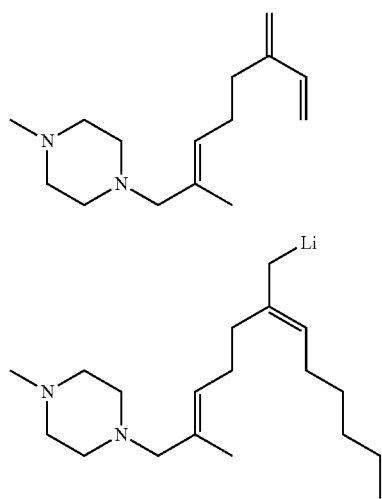

[Formula 1-5]

[Formula i]

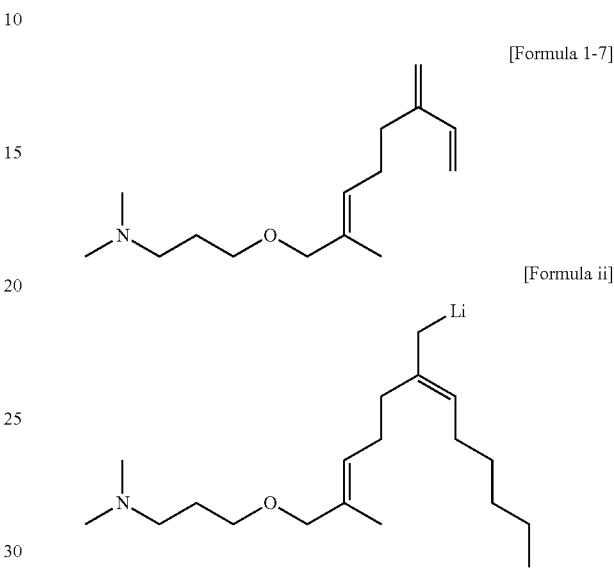

[Formula 1-7]

[Formula ii]

EXAMPLE 7

Two 2 L, vacuum dried stainless steel pressure vessels were prepared. To the first pressure vessel, 1609 g of hexane, 1484 g of a compound represented by Formula 1-7 below, and 103 g of tetramethylethylenediamine were injected to prepare a first reactant. At the same time, to the second pressure vessel, 280 g of 2.5 M n-butyllithium of a liquid phase (in hexane) and 1580 g of hexane were injected to prepare a second reactant. In this case, a molar ratio of the compound represented by Formula 1-7, n-butyllithium and tetramethylethylenediamine was 1:1:1.4. In a state of maintaining the pressure of each pressure vessel to 5 bar, into the continuous type reactor using a mass flowmeter, the first reactant was injected via a first continuous type channel in an injection rate of 1.0 g/min and the second reactant was injected via a second continuous type channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula ii below. The synthesis of the modification polymerization initiator thus prepared was confirmed by the change of molecular weights between the compound represented by Formula 1-7 and a finally

EXAMPLE 8

Two 2 L, vacuum dried stainless steel pressure vessels were prepared. To the first pressure vessel, 1609 g of hexane, 1383 g of a compound represented by Formula 1-6 below, and 103 g of tetramethylethylenediamine were injected to prepare a first reactant. At the same time, to the second pressure vessel, 280 g of 2.5 M n-butyllithium of a liquid phase (in hexane) and 1580 g of hexane were injected to prepare a second reactant. In this case, a molar ratio of the compound represented by Formula 1-6, n-butyllithium and tetramethylethylenediamine was 1:1:1.4. In a state of maintaining the pressure of each pressure vessel to 5 bar, into the continuous type reactor using a mass flowmeter, the first reactant was injected via a first continuous type channel in an injection rate of 1.0 g/min and the second reactant was injected via a second continuous type channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula iii below. The synthesis of the modification polymerization initiator thus prepared was confirmed by the change of molecular weights between the compound represented by Formula 1-6 and a finally obtained material through GC/MS analysis. From MS analysis results, m/z=279 g/mol, and the molecular weight of the compound represented by Formula 1-6 as a starting material was 221 g/mol. In this case, the GC/MS analysis results of the modification polymerization initiator represented that Li in the modification polymerization initiator was substituted with H. GC/MS analysis was performed by the same method as in Example 1.

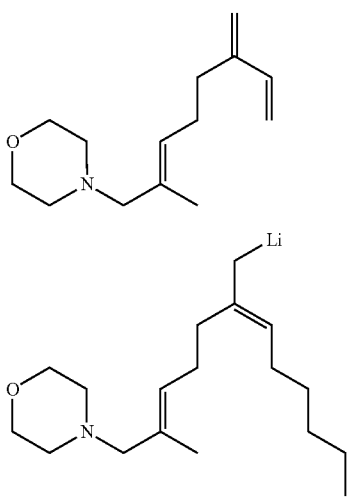

EXAMPLE 9

Two 2 L, vacuum dried stainless steel pressure vessels were prepared. To the first pressure vessel, 1609 g of hexane, 1121 g of a compound represented by Formula 1-1 below, and 103 g of tetramethylethylenediamine were injected to prepare a first reactant. At the same time, to the second pressure vessel, 280 g of 2.5 M n-butyllithium of a liquid phase (in hexane) and 1580 g of hexane were injected to prepare a second reactant. In this case, a molar ratio of the compound represented by Formula 1-1, n-butyllithium and tetramethylethylenediamine was 1:1:1.4. In a state of maintaining the pressure of each pressure vessel to 5 bar, into the continuous type reactor using a mass flowmeter, the first reactant was injected via a first continuous type channel in an injection rate of 1.0 g/min and the second reactant was injected via a second continuous type channel in an injection rate of 1.0 g/min, respectively. After that, the reaction was performed for 5 minutes while maintaining the temperature of the continuous type reactor to 25° C. and the internal pressure to 2 bar using a backpressure regulator to prepare a modification polymerization initiator including a compound represented by Formula iv below. The synthesis of the modification polymerization initiator thus prepared was confirmed by the change of molecular weights between the compound represented by Formula 1-1 and a finally obtained material through GC/MS analysis. From MS analysis results, m/z=237 g/mol, and the molecular weight of the compound represented by Formula 1-1 as a starting material was 179 g/mol. In this case, the GC/MS analysis results of the modification polymerization initiator represented that Li in the modification polymerization initiator was substituted with H. GC/MS analysis was performed by the same method as in Example 1.

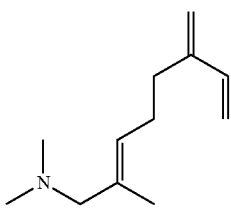

[Formula 1-1]

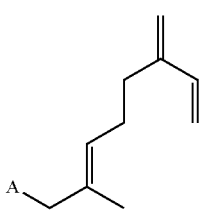

[Formula iv]

EXAMPLE 10 TO EXAMPLE 18

Modified conjugated diene-based polymers including a functional group derived from the modification polymerization initiator, were prepared using the modification polymerization initiators prepared in Example 1 to Example 9, respectively.

Into a 20 L, autoclave reactor, 21 g of styrene, 58 g of 1,3-butadiene and 581 g of n-hexane were injected in the presence of each of the modification polymerization initiators prepared in Example 1 to Example 5, followed by performing polymerization while elevating the temperature from 50° C. to 80° C. until a polymerization conversion ratio reached 99%. Then, a small amount of 1,3-butadiene was injected for capping the terminal of a polymer with butadiene, and 14 g of a solution in which 30 wt % of Wingstay K antioxidant was dissolved in hexane was added. The polymer thus obtained was put in hot water heated with steam, stirred to remove solvents, and roll-dried to remove a remaining amount of the solvent and water to prepare a modified conjugated diene-based copolymer. Elementary analysis on each copolymer thus prepared was performed to confirm that a nitrogen atom was present in a copolymer chain.

The invention claimed is:
1. A modification polymerization initiator, comprising at least one derived unit from a compound represented by the following Formula 1 and a derived unit from a compound represented by the following Formula 2:

[Formula 1]

in Formula 1,
A is $-NR_aR_b$, $-OR_c$, or $-SR_d$, and
$R_a$ to $R_d$ are each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of $R_a$ to $R_d$ is unsubstituted or substituted with a substituent comprising one or more heteroatoms selected among N, O, S, Si and F atoms, and $R_a$ and $R_b$ are optionally combined with each other to form an aliphatic hydrocarbon ring of 5 to 20 carbon atoms, an aromatic hydrocarbon ring of 5 to 20 carbon atoms, or a heterocycle of 3 to 20 carbon atoms, which is unsubstituted or substituted with an alkyl group of 1 to 30 carbon atoms,

[Formula 2]

in Formula 2,

M is an alkali metal, and $R_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

2. The modification polymerization initiator according to claim 1, wherein in Formula 1, A is selected from substituents represented by the following Formula 1a to Formula 1c:

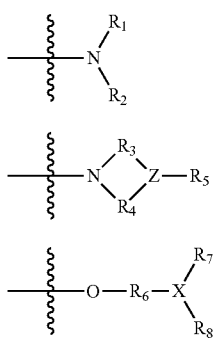

[Formula 1a]

[Formula 1b]

[Formula 1c]

in Formula 1a to Formula 1c, $R_1$, $R_2$, $R_5$, $R_7$ and $R_8$ are each independently an alkyl group of 1 to 10 carbon atoms, an alkenyl group of 2 to 10 carbon atoms, an alkynyl group of 2 to 10 carbon atoms, a cycloalkyl group of 3 to 10 carbon atoms, an aryl group of 6 to 10 carbon atoms, a heteroalkyl group of 1 to 10 carbon atoms, a heteroalkenyl group of 2 to 10 carbon atoms, a heteroalkynyl group of 2 to 10 carbon atoms, a heterocycloalkyl group of 3 to 10 carbon atoms, or a heteroaryl group of 3 to 10 carbon atoms, where $R_1$ and $R_2$, and $R_7$ and $R_8$ are each independently optionally combined to form an aliphatic hydrocarbon ring of 5 to 20 carbon atoms or an aromatic hydrocarbon ring of 6 to 20 carbon atoms, and each of $R_1$, $R_2$, $R_5$, $R_7$ and $R_8$ is independently optionally unsubstituted or substituted with a substituent comprising one or more heteroatoms selected among N, O and S atoms, $R_3$, $R_4$ and $R_6$ are each independently an alkylene group of 1 to 10 carbon atoms, which is unsubstituted or substituted with a substituent comprising an alkyl group of 1 to 10 carbon atoms, a cycloalkyl group of 5 to 10 carbon atoms, an aryl group of 6 to 10 carbon atoms, or a heteroatom selected among N and O atoms, and X and Z are each independently selected among N, O and S atoms, where if X is O or S, $R_8$ is not present, and if Z is O or S, $R_5$ is not present.

3. The modification polymerization initiator according to claim 2, wherein $R_1$, $R_2$, $R_5$, $R_7$ and $R_8$ are each independently an alkyl group of 1 to 10 carbon atoms, which is unsubstituted or substituted with a substituent comprising one or more heteroatoms selected among N, O and S atoms, where $R_1$ and $R_2$, and $R_7$ and $R_8$ are each independently combined to form an aliphatic hydrocarbon ring of 5 to 10 carbon atoms or an aromatic hydrocarbon ring of 6 to 10 carbon atoms, $R_3$, $R_4$ and $R_6$ are each independently an alkylene group of 1 to 10 carbon atoms, which is unsubstituted or substituted with an alkyl group of 1 to 6 carbon atoms, $R_5$ is an alkyl group of 1 to 10 carbon atoms, and X and Z are one selected among N, O and S atoms, where if X is O or S, $R_8$ is not present, and if Z is O or S, $R_5$ is not present.

4. The modification polymerization initiator according to claim 1, wherein the compound represented by Formula 1 is a compound represented by the following Formula 1-1 to Formula 1-11:

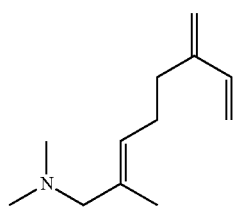
[Formula 1-1]

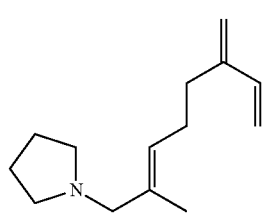
[Formula 1-2]

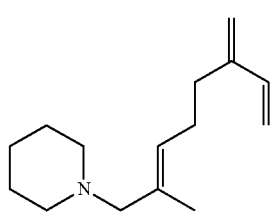
[Formula 1-3]

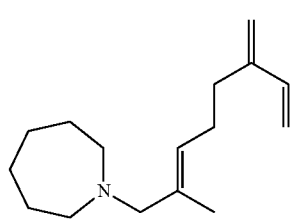
[Formula 1-4]

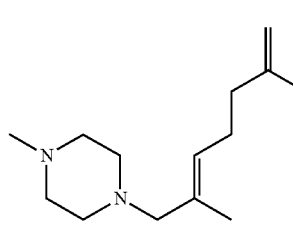
[Formula 1-5]

-continued

[Formula 1-6]
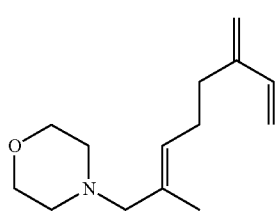

[Formula 1-7]
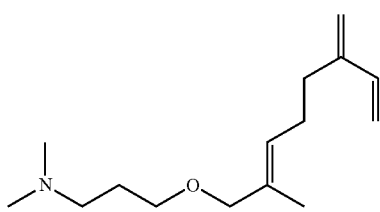

[Formula 1-8]
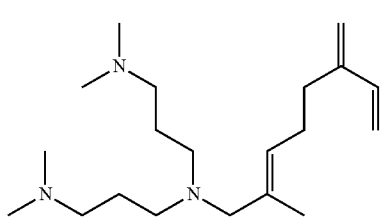

[Formula 1-9]
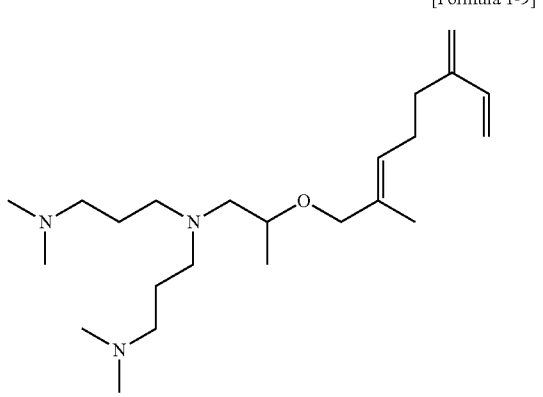

[Formula 1-10]
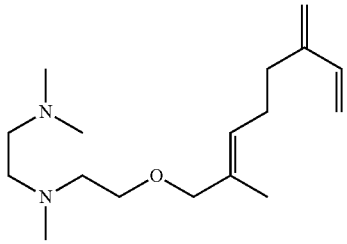

[Formula 1-11]
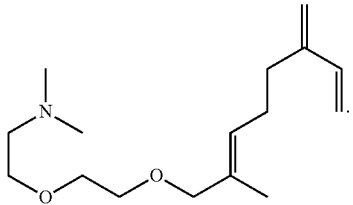

5. The modification polymerization initiator according to claim 1, wherein
in Formula 2, $R_e$ is hydrogen, an alkyl group of 1 to 10 carbon atoms, an alkenyl group of 2 to 10 carbon atoms, an alkynyl group of 2 to 10 carbon atoms, a cycloalkyl group of 5 to 10 carbon atoms or an aryl group of 6 to 10 carbon atoms.

6. The modification polymerization initiator according to claim 1, wherein
the modification polymerization initiator comprises one or more selected from a compound represented by the following Formula 3 or isomers thereof:

[Formula 3]
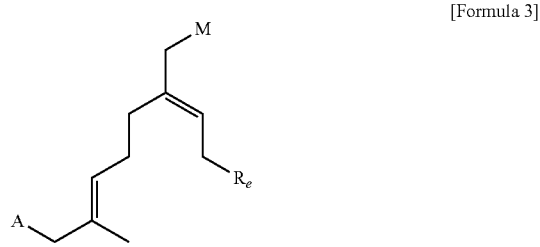

in Formula 3,
A is the same as defined in Formula 1,
M is Na, K or Li, and
$R_e$ is hydrogen or an alkyl group of 1 to 10 carbon atoms.

7. The modification polymerization initiator according to claim 6, wherein the isomer comprises a compound represented by the following Formula 3-1 to Formula 3-3:

[Formula 3-1]
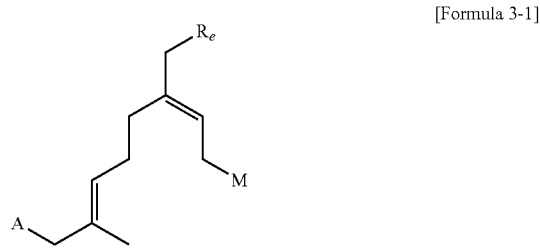

[Formula 3-2]
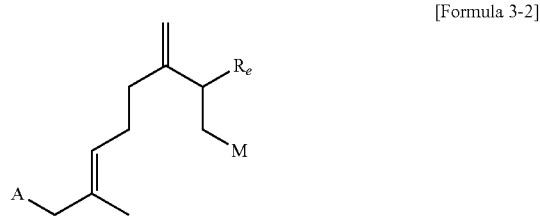

[Formula 3-3]
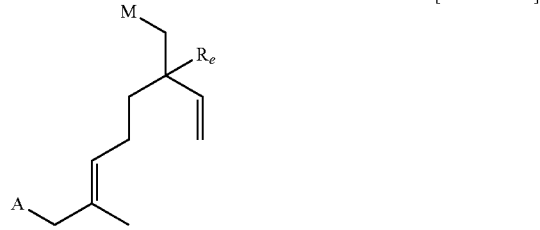

in Formula 3-1 to Formula 3-3,
A is the same as defined in Formula 1,
M is Na, K or Li, and
$R_e$ is hydrogen or an alkyl group of 1 to 10 carbon atoms.

8. The modification polymerization initiator according to claim 6, wherein
the modification polymerization initiator comprises one or more selected among a dimer, a trimer or an oligomer of each of the compound represented by Formula 3 or an isomer thereof.

9. A method for preparing the modification polymerization initiator described in claim 1, the method comprising a step of reacting a compound represented by the following Formula 1 and a compound represented by the following Formula 2:

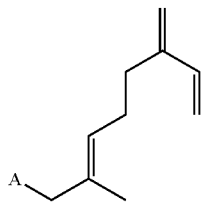

[Formula 1]

in Formula 1,
A is $-NR_aR_b$, $-OR_c$, or $-SR_d$, and
$R_a$ to $R_d$ are each independently an alkyl group of 1 to 30 carbon atoms, an alkenyl group of 2 to 30 carbon atoms, an alkynyl group of 2 to 30 carbon atoms, a cycloalkyl group of 3 to 30 carbon atoms, an aryl group of 6 to 30 carbon atoms, a heteroalkyl group of 1 to 30 carbon atoms, a heteroalkenyl group of 2 to 30 carbon atoms, a heteroalkynyl group of 2 to 30 carbon atoms, a heterocycloalkyl group of 2 to 30 carbon atoms or a heteroaryl group of 3 to 30 carbon atoms, where each of $R_a$ to $R_d$ is independently unsubstituted or substituted with a substituent comprising one or more heteroatoms selected among N, O, S, Si and F atoms, and $R_a$ and $R_b$ are optionally combined with each other to form an aliphatic hydrocarbon ring of 5 to 20 carbon atoms, an aromatic hydrocarbon ring of 6 to 20 carbon atoms, or a heterocycle of 3 to 20 carbon atoms, which is unsubstituted or substituted with an alkyl group of 1 to 30 carbon atoms, $M^+$—$R_e^-$  [Formula 2]

in Formula 2,
M is an alkali metal, and
$R_e$ is hydrogen, an alkyl group of 1 to 30 carbon atoms, an alkenyl group of 2 to 30 carbon atoms, an alkynyl group of 2 to 30 carbon atoms, a cycloalkyl group of 5 to 30 carbon atoms, or an aryl group of 6 to 30 carbon atoms.

10. The method for preparing the modification polymerization initiator according to claim 9, wherein
in Formula 1, A is selected from substituents represented by the following Formula 1a to Formula 1c, and
in Formula 2, $R_e$ is hydrogen, an alkyl group of 1 to 10 carbon atoms, an alkenyl group of 2 to 10 carbon atoms, an alkynyl group of 2 to 10 carbon atoms, a cycloalkyl group of 5 to 10 carbon atoms, or an aryl group of 6 to 10 carbon atoms:

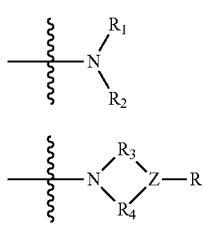

[Formula 1a]

[Formula 1b]

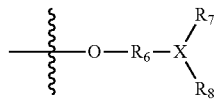

[Formula 1c]

in Formula 1a to Formula 1c,
$R_1$, $R_2$, $R_5$, $R_7$ and $R_8$ are each independently an alkyl group of 1 to 10 carbon atoms, an alkenyl group of 2 to 10 carbon atoms, an alkynyl group of 2 to 10 carbon atoms, a cycloalkyl group of 3 to 10 carbon atoms, an aryl group of 3 to 10 carbon atoms, a heteroalkyl group of 1 to 10 carbon atoms, a heteroalkenyl group of 2 to 10 carbon atoms, a heteroalkynyl group of 2 to 10 carbon atoms, a heterocycloalkyl group of 3 to 10 carbon atoms, or a heteroaryl group of 3 to 10 carbon atoms, where $R_1$ and $R_2$, and $R_7$ and $R_8$ are each independently optionally combined to form an aliphatic hydrocarbon ring of 5 to 20 carbon atoms or an aromatic hydrocarbon ring of 6 to 20 carbon atoms, and each of $R_1$, $R_2$, $R_5$, $R_7$ and $R_8$ is independently unsubstituted or substituted with a substituent comprising one or more heteroatoms selected among N, O and S atoms,
$R_3$, $R_4$ and $R_6$ are each independently an alkylene group of 1 to 10 carbon atoms, which is unsubstituted or substituted with a substituent comprising an alkyl group of 1 to 10 carbon atoms, a cycloalkyl group of 5 to 10 carbon atoms, an aryl group of 5 to 10 carbon atoms, or a heteroatom selected among N and O atoms, and
X and Z are each independently one selected among N, O and S atoms, where if X is O or S, $R_8$ is not present, and if Z is O or S, $R_5$ is not present.

11. The method for preparing the modification polymerization initiator according to claim 9, wherein
the reaction is performed in a continuous reactor comprising a first continuous channel and a second continuous channel, and
prior to performing the reaction, a first reactant comprising the compound represented by Formula 1 is injected through the first continuous channel to the continuous reactor, and a second reactant comprising the compound represented by Formula 2 is injected through the second continuous channel to the continuous reactor.

12. The method for preparing the modification polymerization initiator according to claim 9, wherein
the compound represented by Formula 1 and the compound represented by Formula 2 are reacted in a molar ratio of 1:0.5 to 5.0.

13. The method for preparing the modification polymerization initiator according to claim 9, wherein
the reaction is performed in a temperature range of 0° C. to 80° C. and pressure conditions of 0.5 bar to 10 bar.

14. The method for preparing the modification polymerization initiator according to claim 9, wherein
the reaction is performed in the presence of a polar additive, and
the polar additive comprises one or more selected from tetrahydrofuran, ditetrahydrofurylpropane, diethyl ether, cycloamyl ether, dipropyl ether, ethylene dimethyl ether, ethylene diethyl ether, diethyl glycol, dimethyl glycol, tert-butoxyethoxyethane, bis(3-dimethylamino ethyl) ether, (dimethylamino ethyl) ethyl ether, trimethylamine, triethylamine, tripropylamine or tetramethylethylenediamine.

15. The method for preparing the modification polymerization initiator according to claim 11, wherein
the first reactant is injected through the first continuous channel in a rate of 1.0 g/min to 20.0 g/min to the continuous reactor, and
the second reactant is injected through the second continuous channel in a rate of 1.0 g/min to 20.0 g/min to the continuous reactor.

* * * * *